(12) United States Patent
Vidal et al.

(10) Patent No.: US 9,296,683 B2
(45) Date of Patent: Mar. 29, 2016

(54) PROCESS FOR PREPARING ESTERAMIDE COMPOUNDS

(75) Inventors: Thierry Vidal, Lyons (FR); Rabih Rached, Millery (FR); Massimo Guglieri, Anhangabau-Jundiai (BR)

(73) Assignee: RHODIA OPERATIONS, Aubervilliers (FR)

( * ) Notice: Subject to any disclaimer, the term of this patent is extended or adjusted under 35 U.S.C. 154(b) by 191 days.

(21) Appl. No.: 13/702,453

(22) PCT Filed: May 31, 2011

(86) PCT No.: PCT/EP2011/058985
§ 371 (c)(1),
(2), (4) Date: Apr. 22, 2013

(87) PCT Pub. No.: WO2011/154292
PCT Pub. Date: Dec. 15, 2011

(65) Prior Publication Data
US 2013/0211129 A1     Aug. 15, 2013

(30) Foreign Application Priority Data
Jun. 9, 2010 (FR) .................................... 10 54536

(51) Int. Cl.
C07C 231/02 (2006.01)
(52) U.S. Cl.
CPC .................................... *C07C 231/02* (2013.01)
(58) Field of Classification Search
CPC .................................................... C07C 231/02
USPC ........................................................ 560/155
See application file for complete search history.

(56) References Cited

U.S. PATENT DOCUMENTS

| 3,288,794 A | 11/1966 | Kuceski |
| 3,417,114 A | 12/1968 | Kuceski |
| 4,588,833 A | 5/1986 | Kadelka et al. |
| 5,235,093 A * | 8/1993 | Cova et al. .................. 560/155 |
| 2011/0166025 A1 | 7/2011 | Jentzer et al. |

FOREIGN PATENT DOCUMENTS

| CN | 101050206 | * 10/2007 |
| WO | WO2010/151791 | * 12/2010 |

OTHER PUBLICATIONS

Zradni et al., "Synthesis of Amides from Esters and Amines Under Microwave Irradiation," Synthetic Communications, 32(22), 3525-3531, 2002.*
Translation of CN101050206, Oct. 2007.*
International Preliminary Report on Patentabilty for PCT/EP2011/058985 dated Dec. 10, 2012.
International Search Report for PCT/EP2011/058985 dated Aug. 1, 2011.

* cited by examiner

*Primary Examiner* — Paul A Zucker
*Assistant Examiner* — Mark Luderer
(74) *Attorney, Agent, or Firm* — B. Aaron Schulman, Esq.; Stites & Harbison, PLLC

(57) ABSTRACT

The present invention concerns a process for preparing esteramide compounds. More particularly, the invention relates to a process for preparing esteramide compounds by reaction between a diester and an amine, in the presence of a basic compound, wherein the basic compound and the amine in gaseous form are co-added to the diester, the reaction being conducted at a temperature of 30° C. or higher.

27 Claims, No Drawings

PROCESS FOR PREPARING ESTERAMIDE COMPOUNDS

The present invention concerns a process for preparing esteramide compounds.

More particularly, the invention relates to a process for preparing esteramide compounds by reaction between a diester and an amine.

Esteramide compounds are known for their applications as solvents in particular for plant health applications as described for example in document WO 2009/092795.

Several routes can be used to access the said esteramide compounds.

Document U.S. Pat. No. 4,588,833 describes a method for preparing esteramides by the cobalt-catalysed reaction of an unsaturated amide with an alcohol and carbon monoxide, at high temperature.

Document U.S. Pat. No. 3,417,114, in Example 9, describes a method for the simultaneous preparation of a « DMGME» esteramide compound of formula: MeOOC—$(CH_2)_3$—$CONMe_2$ and of a « TMG» diamide compound of formula: $Me_2NOC$—$(CH_2)_3$—$CONMe_2$, followed by the separation via distillation of these two compounds. To conduct the reaction, gaseous dimethylamine is bubbled for 2 h in a medium comprising previously purified dimethyl glutarate and a solution of sodium methylate. The two compounds (DMGME and TMG) are then isolated by distillation from the complex mixture obtained.

Document U.S. Pat. No. 3,288,794 describes the same method as document U.S. Pat. No. 3,417,114 and the simultaneous preparation of a methyl ester of N,N-dimethyl-adipamide and N,N,N',N'-tetramethyl-adipamide using a similar operating mode, also followed by separation via distillation.

Concerning diesters, the above-described methods of the prior art are not esteramide-selective. The proportion of diamide is often a majority proportion and the esteramide is considered to be a by-product which has not fully reacted.

In addition, for such methods, a purification step of the diester prior to the reaction is necessary, which complicates the process.

This type of process also requires cumbersome and costly treatment of the reaction medium after the reaction to isolate the diamide and the esteramide e.g. via distillations.

Also, with these prior art methods, the crude products formed may have a strong orange-yellow colouring which is detrimental for subsequent uses. The products are therefore subjected to additional purification steps. All these purification treatments make esteramide production processes a complex operation.

In an attempt to overcome the problem of low esteramide selectivity, it is frequent to operate at low temperatures i.e. lower than ambient temperature, by cooling the reaction medium. However, the lowering of the reaction temperature significantly reduces the kinetics of the reaction and hence the productivity of the method.

There is therefore a need to find a process for producing esteramide compounds from diesters which is esteramide-selective. In addition, the process must be easy to implement in an industrial installation. Another essential need of the process is that the reaction must have fast kinetics. Finally, the esteramide manufacturing process must be productive.

For this purpose, the present invention proposes a process for preparing an esteramide compound of following formula (I):

$$R^1OOC\text{-}A\text{-}CONR^2R^3 \tag{I}$$

comprising a reaction step between:
a diester compound of following formula (II):

$$R^1OOC\text{-}A\text{-}COOR^1 \tag{II}$$

and an amine of following formula (III):

$$HNR^2R^3 \tag{III}$$

in the presence of a basic compound,
formulae in which:
- A is a covalent bond or a straight-chain or branched divalent alkylene group comprising a number of carbon atoms ranging from 1 to 12,
- $R^1$ is a hydrocarbon group, optionally substituted, comprising from 1 to 36 carbon atoms,
- $R^2$ and $R^3$, the same or different, are groups chosen from among the hydrogen atom and the hydrocarbon groups, optionally substituted, comprising from 1 to 36 carbon atoms,
- $R^2$ and $R^3$ are able together to form a ring comprising the nitrogen atom with which they are linked, the said ring optionally being substituted and/or comprising an additional heteroatom, and
- $R^2$ and $R^3$ not simultaneously being hydrogen atoms, characterized by the fact that:
- the amine of formula (III) in gaseous form and the basic compound are co-added to the diester compound of formula (II),
- and the reaction is conducted at a temperature of 30° C. or higher.

By « are co-added» in the meaning of the present invention is that the compounds are added to the diester compound (II) simultaneously but via independent feeds. By « simultaneously» is meant that the compounds at least have one common addition time, the addition possibly starting and ending at different times for each compound. Preferably, the addition of the two compounds starts at the same time.

According to one advantageous embodiment of the invention, the co-addition time (common period of addition) is between 30 minutes and 6 hours, preferably between 30 minutes and 3 hours and further preferably between 30 minutes and 2 hours.

The process of the invention therefore uses a diester compound of formula (II) which advantageously has the characteristics given below.

According to one advantageous embodiment, in formulae (I) and (II), A is a branched divalent alkylene group comprising a number of carbon atoms ranging from 2 to 12, preferably ranging from 3 to 6 carbon atoms.

Preferably, in formulae (I) and (II), the $R^1$ groups, the same or different, are hydrocarbon groups comprising from 1 to 16 carbon atoms and possibly carrying one or more substituents. By « substituent», as a non-limiting illustration, is meant an alkyl group preferably having from 1 to 4 carbon atoms, an alkoxy group preferably having from 1 to 4 carbon atoms, a hydroxy or halogen group.

Preferably, $R^1$ groups, the same or different, are chosen from the group consisting of the alkyl, alkenyl, cycloalkyl, aryl and arylalkyl groups, the said groups possibly carrying one or more substituents.

More particularly, $R^1$ is preferably chosen from the group consisting of the methyl, ethyl, n-propyl, isopropyl, n-butyl, isobutyl, tertiobutyl, sec-butyl, n-pentyl, isopentyl, sec-pentyl, cyclopentyl, n-hexyl, isohexyl, sec-hexyl, cyclohexyl, methylcyclohexyl, 2-ethylbutyl, 3-methylpentyl, n-heptyl, isoheptyl, sec-heptyl, 3-methylhexyl, 4-methylhexyl, 1-ethylpentyl, 2-ethylpentyl, 3-ethylpentyl, n-octyl, isooctyl, 3-methylheptyl, n-nonyl, n-decyl, undecyl, n-dodecyl, tridecyl, tetradecyl and pentadecyl groups.

In one particularly advantageous embodiment, $R^1$ is chosen from the methyl and ethyl groups. Most preferably, the diester compound of formula (II) is a mixture of diester compounds of following formulae (II.1), (II.2) and (II.3):

$$R^1OOC\text{—}CH(CH_3)\text{—}CH_2\text{—}CH_2\text{—}COOR^1 \quad (II.1)$$

$$R^1OOC\text{—}CH(CH_2\text{—}CH_3)\text{—}CH_2\text{—}COOR^1 \quad (II.2)$$

$$R^1OOC\text{—}CH_2\text{—}CH_2\text{—}CH_2\text{—}CH_2\text{—}COOR^1 \quad (II.3)$$

with $R^1$ such as defined above.

The mixture of diester compounds of formula (II.1), (II.2) and (II.3) may have the following composition:
- from 75 to 95% by weight of the formula (II.1) compound, preferably from 85 to 95% by weight,
- from 3 to 23% by weight of the formula (II.2) compound, preferably from 4 to 14% by weight,
- from 0.1 to 10% by weight of the formula (II.3) compound, preferably from 0.1 to 3% by weight.

It is particularly preferred that, for the mixture of diester compounds of formula (II.1), (II.2) and (II.3) above, the $R^1$ groups should be methyl groups. The mixture may in particular be a mixture of diesters marketed by Rhodia under the trade name Rhodiasolv® IRIS.

According to one advantageous embodiment of the invention, the diester compound (II) is added pure, i.e. it is not placed in solution in an organic solvent. However, it is possible that the diester compound (II) may be placed in solution in an organic solvent. According to one preferred embodiment of the invention, the organic solvent is chosen from among volatile organic solvents, in particular alcohols and ethers, preferably from among methanol, ethanol, tetrahydrofuran (THF) and mixtures thereof. More preferably, the organic solvent is methanol.

Also used in the method of the invention is an amine of formula (III), in gaseous form, which advantageously has the characteristics given below.

Preferably, in formulae (I) and (III), the groups $R^2$ and $R^3$, the same or different, are hydrocarbon groups comprising from 1 to 16 carbon atoms possibly carrying one or more substituents. By «substituent», as a non-limiting illustration, is meant an alkyl group preferably having from 1 to 4 carbon atoms, an alkoxy group preferably having from 1 to 4 carbon atoms, a hydroxy or halogen group.

Preferably, the groups $R^2$ and $R^3$, the same or different, are chosen from the group consisting of the alkyl, alkenyl, cycloalkyl, aryl and arylalkyl groups, the said groups possibly carrying one or more substituents.

According to one first embodiment of the invention $R^2$ and $R^3$, the same or different, are chosen from the group consisting of the methyl, ethyl, hydroxyethyl, n-propyl, isopropyl, n-butyl, isobutyl, tertiobutyl, n-pentyl, isoamyl, hexyl and cyclohexyl groups. Preferably, $R^2$ and $R^3$ are chosen from among the methyl, ethyl and hydroxyethyl groups.

According to a second embodiment of the invention, $R^2$ and $R^3$ together form a ring of 5 or 6 atoms comprising the nitrogen atom with which they are linked, one of the atoms of the ring possibly being another heteroatom, such as oxygen for example. Preferably, $R^2$ and $R^3$ together form a ring chosen from among a morpholine, a piperidine and a piperazine.

The process of the invention uses a basic compound.

Preferably, the basic compound is alkoxide of an alkaline metal or alkaline-earth metal, preferably chosen from among sodium methylate, sodium or potassium ethylate, potassium ter-butylate. The basic compound can also be chosen from the carbonates, in particular potassium or sodium carbonate; or the alkyl titanates e.g. butyl titanate. The basic compound can also be a mixture of several of the above-cited compounds. Preferably, the basic compound is sodium methylate.

According to one preferred embodiment of the invention, the basic compound is in solution in an organic solvent.

In this case, it is the same solvent as the one described above for the diester compound (II), preferably an organic solvent chosen from methanol, ethanol, tetrahydrofuran (THF) and mixtures thereof. Preferably the organic solvent is methanol.

In general, the basic compound is in solution in an organic solvent at a weight concentration in the organic solvent which is advantageously comprised from 5 to 80%, preferably from 10 to 50% and further preferably from 20 to 30%.

According to the invention, the diester compound of formula (II) and the amine of formula (III) are caused to react in the presence of the basic compound, in the proportions defined below.

Advantageously, the added quantity of amine (III) in gaseous form corresponds to a molar ratio relative to the diester compound (II) ranging from 1 to 1.5, preferably from 1 to 1.2 and further preferably from 1 to 1.1.

The basic compound is preferably added at a molar concentration relative to the diester compound (II) comprised from 0.01 to 20%, preferably from 3 to 10%.

According to another characteristic of the invention, the reaction is conducted at a temperature of 30° C. or higher. Preferably, the reaction is conducted at a temperature of 50° C. or higher. Advantageously, the reaction is conducted at a temperature comprised from 30° C. to 130° C., preferably from 40° C. to 90° C. and further preferably from 45° C. to 65° C. The calories required for controlling this temperature are provided either by the reaction itself or by external means, e.g. heating or cooling means.

Advantageously, the reaction is conducted at a pressure comprised from 1 to 10 absolute bars, preferably from 1 to 5 absolute bars and further preferably from 1 to 3 absolute bars.

Preferably, the reaction is conducted under anhydrous conditions i.e. up to 0.2% of water is tolerated, preferably up to 0.05% of water.

According to one preferred embodiment, the reaction is conducted under inert conditions, for example using flushing means with an inert gas, with nitrogen in particular.

From a practical viewpoint, the amine of formula (II) in gaseous form and the basic compound are co-added to the diester compound of formula (II), the temperature being held in the previously defined temperature range.

According to the invention, at the end of the reaction the esteramide compound of formula (I) is obtained. The reaction mixture at the end of the reaction does not require any cumbersome purification of the esteramide compound to separate it from the diamide compound. Only the volatile compounds such as the amine which have not reacted and the solvent can be removed, in particular evaporated e.g. by distillation under reduced pressure. The medium may optionally be treated using conventional operations known to the skilled person, in particular via neutralisation, filtration and washing steps to remove the salts formed during the reaction. The esteramide compound of formula (I) thus obtained is of high purity and can be used directly in applications for which it is intended, for example as solvent, in particular for plant health applications.

The process of the invention may be a continuous or batch process.

The process of the invention has numerous advantages. It is particularly advantageous when used on a mixture of diester compounds meeting formulae (II.1), (II.2) and (II.3), for example Rhodiasolv®IRIS, and at a temperature higher than 30° C.

First, it is highly esteramide-selective i.e. the selectivity for esteramide is higher than 90% even higher than 95%. Surprisingly, less than 5% of diamide is formed despite the excess amine and a reaction temperature of 30° C. or higher. In addition, the process of the invention provides control over the quantity of amine added, by means of bubbling, and over the reaction time. It is therefore not necessary to add amine in excess relative to the diester. The reaction is also very rapid compared with reactions at lower temperature and without excess amine. Indeed, the process of the invention has high reaction kinetics and hence very short reaction times. In addition, no significant colouring is observed and the reaction mixture at the end of the reaction does not require any cumbersome purification treatment of the majority product, thereby largely simplifying the process and increasing its productivity.

The following examples illustrate but do not limit the invention.

EXAMPLES

Example 1, Comparative

Dimethylamine (Gas) on a Rhodiasolv® IRIS/Sodium Methylate Mixture—T=20° C.

In a well-agitated, double-jacketed 1 L reactor equipped with mechanical agitation and previously dried are placed a solution of sodium methylate in methanol (%50 w/w solution, 18.8 g) and 304 g of a mixture of diesters of 2-methyl-glutaric acid, 2-ethyl-succinic acid and adipic acid marketed under the trade name Rhodiasolv® IRIS by Rhodia.

It is ascertained that the reaction medium turns a strong orange-yellow colour.

The temperature of the reaction medium is stabilised at the set point of +20° C. and bubbling of the gaseous dimethylamine is set in operation for 2 hours in the reaction mixture containing the sodium methylate and mixture of diesters (addition of 82 g of dimethylamine). The temperature of the reaction medium is held constant during the bubbling period.

The temperature of the reaction medium is held at +20° C. until 96% of the mixture of diesters initially added has been consumed (completion time: 20 hours).

The slight excess of dimethylamine is distilled under reduced pressure (~200 mbar) at a temperature is comprised from 20° C. to 50° C. The reaction medium is then neutralised through the addition of a sufficient quantity of 85% phosphoric acid. The salts formed are filtered. The solid formed is washed in methanol then the volatile compounds (methanol and non-reacted diester) are vacuum distilled.

The product is then analysed by gas phase chromatography.

Table 1 below groups together the conditions and results of this comparative Example 1.

Example 2, Comparative

Dimethylamine (Gas) on a Rhodiasolv® IRIS/Sodium Methylate Mixture—T=50° C.

In a well-agitated, double-jacketed 1 L reactor equipped with mechanical agitation and previously dried are placed a solution of sodium methylate in methanol (%50 w/w solution, 18.8 g) and 304 g of a mixture of diesters of 2-methyl-glutaric acid, 2-ethyl-succinic acid and adipic acid marketed under the trade name Rhodiasolv® IRIS by Rhodia.

It is ascertained that the reaction medium turns a strong orange-yellow colour.

The temperature of the reaction medium is stabilised at the set point of +50° C. and bubbling of the gaseous dimethylamine is set in operation for 2 hours in the reaction mixture containing the sodium methylate and the mixture of diesters (addition of 82 g of dimethylamine). The temperature of the reaction medium is held constant throughout the bubbling period.

The temperature of the reaction medium is held at +50° C. until 96% of the mixture of diesters initially added has been consumed (completion time: 2 hours).

The slight excess of dimethylamine is distilled under reduced pressure (~200 mbar) at a temperature comprised from 20° C. to 50° C. The reaction medium is then neutralised through the addition of a sufficient amount of 85% phosphoric acid. The salts formed are filtered. The solid formed is washed in methanol then the volatile compounds (methanol and non-reacted diester) are vacuum distilled.

The product is then analysed by gas phase chromatography.

Table 1 below groups together the conditions and results of this comparative Example 2.

Example 3

Dimethylamine (gas) and Sodium Methylate Co-Added to Rhodiasolv® IRIS

In a well-agitated, double-jacketed 1 L reactor equipped with mechanical stirring and previously dried are placed 304 g of a mixture of diesters of 2-methyl-glutaric acid, 2-ethyl-succinic acid and adipic acid marketed under the trade name Rhodiasolv® IRIS by Rhodia.

No significant colouring of the reaction medium is ascertained.

The temperature of the reaction medium is stabilised at the set point of +50° C. and the co-addition is made of gaseous dimethylamine (bubbling in the diester—addition of 82 g dimethylamine) and a solution of sodium methylate in methanol (drop addition—%50 w/w solution, 18.8 g).

The duration of the co-addition is 2 hours. The temperature of the reaction medium is held constant throughout the co-addition time.

The temperature of the reaction medium is held at +50° C. until 96% of the mixture of diesters initially added has been consumed (completion time: 2 hours).

The slight excess of dimethylamine is distilled under reduced pressure (~200 mbar) at a temperature of between 20 and 50° C. The reaction medium is then neutralised through the addition of a sufficient amount of 85% phosphoric acid. The salts formed are filtered. The solid formed is washed in methanol then the volatile compounds (methanol and non-reacted diester) are vacuum distilled.

The product is then analysed by gas phase chromatography.

Table 1 below groups together the conditions and results of the different Examples 1C, 2C and 3.

TABLE 1

| Test | T (° C.) | Time (h) [a] | Esteramide (%) [b] | Diamide (%) [b] | Di/EA (%) [c] | Colouring of crude reaction medium |
|---|---|---|---|---|---|---|
| 1C | 20 | 20 | 95 | 3 | 3.1 | Orange-yellow |
| 2C | 50 | 2 | 96.3 | 3.7 | 3.8 | Orange-yellow |
| 3 | 50 | 2 | 96.5 | 2.9 | 3.0 | no colouring |

[a] Time needed for completion of the reaction
[b] Species content given at the end of treatment
[c] Di/EA = ratio of final diamide/esteramide concentrations It follows from the above Examples that, surprisingly, the process of the invention (Example 3) is highly esteramide-selective (96.5%) and that less than 3% of diamide are formed. In addition, the reaction of the invention is very rapid (2 h) and the product obtained has no colouring, which allows direct use thereof, without any additional purification step, contrary to the methods in the comparative Examples.

The invention claimed is:

1. A process for preparing an esteramide compound of following formula (I):

$$R^1OOC\text{-}A\text{-}CONR^2R^3 \quad (I)$$

comprising a reaction step between:
a diester compound of following formula (II):

$$R^1OOC\text{-}A\text{-}COOR^1 \quad (II)$$

and an amine of following formula (III):

$$HNR^2R^3 \quad (III)$$

in the presence of a basic compound,
formulae in which:
A is a covalent bond or a straight-chain or branched divalent alkylene group comprising a number of carbon atoms ranging from 1 to 12,
$R^1$ is an optionally substituted hydrocarbon group, comprising from 1 to 36 carbon atoms,
$R^2$ and $R^3$, the same or different, are groups chosen from the hydrogen atom and the hydrocarbon groups, optionally substituted, comprising from 1 to 36 carbon atoms,
$R^2$ and $R^3$ are able together to form a ring comprising the nitrogen atom with which they are linked, the said ring optionally being substituted and/or comprising an additional heteroatom, and
$R^2$ and $R^3$ not simultaneously being hydrogen atoms,
wherein:
the amine of formula (III) in gaseous form and the basic compound are co-added to the diester compound of formula (II),
and the reaction is conducted at a temperature of 30° C. or higher;
wherein the diester compound of formula (II) is a mixture of diester compounds of following formulae (II.1), (II.2) and (II.3):

$$R^1OOC\text{---}CH(CH_3)\text{---}CH_2\text{---}CH_2\text{---}COOR^1 \quad (II.1)$$

$$R^1OOC\text{---}CH(CH_2\text{---}CH_3)\text{---}CH_2\text{---}COOR^1 \quad (II.2)$$

$$R^1OOC\text{---}CH_2\text{---}CH_2\text{---}CH_2\text{---}CH_2\text{---}COOR^1 \quad (II.3).$$

2. The process according to claim 1, wherein the $R^1$ groups, the same or different, are hydrocarbon groups comprising from 1 to 16 carbon atoms optionally carrying one or more substituents.

3. The process according to claim 1, wherein the $R^1$ groups, the same or different, are chosen from the group consisting of the alkyl, alkenyl, cycloalkyl, aryl and arylalkyl groups, the said groups optionally carrying one or more substituents.

4. The process according to claim 1, wherein $R^1$ is chosen from the group consisting of the methyl, ethyl, n-propyl, isopropyl, n-butyl, isobutyl, tertiobutyl, sec-butyl, n-pentyl, isopentyl, sec-pentyl, cyclopentyl, n-hexyl, isohexyl, sec-hexyl, cyclohexyl, methylcyclohexyl, 2-ethylbutyl, 3-methylpentyl, n-heptyl, isoheptyl, sec-heptyl, 3-methylhexyl, 4-methylhexyl, 1-ethylpentyl, 2-ethylpentyl, 3-ethylpentyl, n-octyl, isooctyl, 3-methylheptyl, n-nonyl, n-decyl, undecyl, n-dodecyl, tridecyl, tetradecyl and pentadecyl groups.

5. The process according to claim 1, wherein the mixture of diester compounds of formula (II.1), (II.2) and (II.3) has the following composition:
from 75 to 95% by weight of the formula (II.1) compound,
from 3 to 23% by weight of the formula (II.2) compound, and
from 0.1 to 10% by weight of the formula (II.3) compound.

6. The process according to claim 1, wherein the $R^1$ groups are methyl groups.

7. The process according to claim 1, wherein the groups $R^2$ and $R^3$, the same or different, are chosen from the group consisting of the alkyl, alkenyl, cycloalkyl, aryl and arylalkyl groups, the said groups optionally carrying one or more substituents.

8. The process according to claim 7, wherein $R^2$ and $R^3$, the same or different, are chosen from the group consisting of the methyl, ethyl, hydroxyethyl, n-propyl, isopropyl, n-butyl, isobutyl, tertiobutyl, n-pentyl, isoamyl, hexyl and cyclohexyl groups.

9. The process according to claim 1, wherein $R^2$ and $R^3$ together form a ring with 5 to 6 atoms, comprising the nitrogen atom with which they are linked, one of the atoms of the ring optionally being another heteroatom.

10. The process according to claim 9, wherein $R^2$ and $R^3$ together form a ring chosen from morpholine, piperidine and piperazine.

11. The process according to claim 1, wherein the basic compound is an alkoxide of an alkaline metal or alkaline-earth metal; potassium or sodium carbonate, alkyl titanates and mixtures thereof.

12. The process according to claim 1, wherein the basic compound is in solution in an organic solvent.

13. The process according to claim 12, wherein the organic solvent is chosen from alcohols and ethers, and mixtures thereof.

14. The process according to claim 1, wherein the added quantity of amine (III) in gaseous form corresponds to a molar ratio relative to the diester compound (II) ranging from 1 to 1.5.

15. The process according to claim 1, wherein the basic compound is added at a molar concentration relative to the diester compound comprised from 0.01 to 20%.

16. The process according to claim 1, wherein the reaction is conducted at a temperature comprised from 30° C. to 130° C.

17. The process according to claim 1, wherein the reaction is conducted at a temperature comprised from 40° C. to 90° C.

18. The process according to claim 1, wherein the reaction is conducted at a temperature comprised from 45° C. to 65° C.

19. A process for preparing an esteramide compound of following formula (I):

$$R^1OOC\text{-}A\text{-}CONR^2R^3 \quad (I)$$

comprising a reaction step between:
a diester compound of following formula (II):

$$R^1OOC\text{-}A\text{-}COOR^1 \quad (II)$$

and an amine of following formula (III):

$$HNR^2R^3 \quad (III)$$

in the presence of a basic compound,
formulae in which:
- A is a covalent bond or a straight-chain or branched divalent alkylene group comprising a number of carbon atoms ranging from 1 to 12,
- $R^1$ is an optionally substituted hydrocarbon group, comprising from 1 to 36 carbon atoms,
- $R^2$ and $R^3$, the same or different, are groups chosen from the hydrogen atom and the hydrocarbon groups, optionally substituted, comprising from 1 to 36 carbon atoms,
- $R^2$ and $R^3$ are able together to form a ring comprising the nitrogen atom with which they are linked, the said ring optionally being substituted and/or comprising an additional heteroatom, and
- $R^2$ and $R^3$ not simultaneously being hydrogen atoms, wherein:
the amine of formula (III) in gaseous form and the basic compound are co-added to the diester compound of formula (II),
and the reaction is conducted at a temperature of 30° C. or higher; and
wherein the added quantity of amine (III) in gaseous form corresponds to a molar ratio relative to the diester compound (II) ranging from 1 to 1.5.

20. The process according to claim 19, wherein the diester compound of formula (II) is a mixture of diester compounds of following formulae (II.1), (II.2) and (II.3):

$$R^1OOC-CH(CH_3)-CH_2-CH_2-COOR^1 \quad (II.1)$$

$$R^1OOC-CH(CH_2-CH_3)-CH_2-COOR^1 \quad (II.2)$$

$$R^1OOC-CH_2-CH_2-CH_2-CH_2-COOR^1 \quad (II.3).$$

21. The process according to claim 19, wherein the mixture of diester compounds of formula (II.1), (II.2) and (II.3) has the following composition:
from 75 to 95% by weight of the formula (II.1) compound,
from 3 to 23% by weight of the formula (II.2) compound,
from 0.1 to 10% by weight of the formula (II.3) compound.

22. A process for preparing an esteramide compound of following formula (I):

$$R^1OOC-A-CONR^2R^3 \quad (I)$$

comprising a reaction step between:
a diester compound of following formula (II):

$$R^1OOC-A-COOR^1 \quad (II)$$

and an amine of following formula (III):

$$HNR^2R^3 \quad (III)$$

in the presence of a basic compound,
formulae in which:
- A is a covalent bond or a straight-chain or branched divalent alkylene group comprising a number of carbon atoms ranging from 1 to 12,
- $R^1$ is an optionally substituted hydrocarbon group, comprising from 1 to 36 carbon atoms,
- $R^2$ and $R^3$, the same or different, are groups chosen from the hydrogen atom and the hydrocarbon groups, optionally substituted, comprising from 1 to 36 carbon atoms,
- $R^2$ and $R^3$ are able together to form a ring comprising the nitrogen atom with which they are linked, the said ring optionally being substituted and/or comprising an additional heteroatom, and
- $R^2$ and $R^3$ not simultaneously being hydrogen atoms, wherein:
the amine of formula (III) in gaseous form and the basic compound are co-added to the diester compound of formula (II),
and the reaction is conducted at a temperature of 30° C. or higher; and
wherein the basic compound is added at a molar concentration relative to the diester compound comprised from 0.01 to 20%.

23. The process according to claim 22, wherein the diester compound of formula (II) is a mixture of diester compounds of following formulae (II.1), (II.2) and (II.3):

$$R^1OOC-CH(CH_3)-CH_2-CH_2-COOR^1 \quad (II.1)$$

$$R^1OOC-CH(CH_2-CH_3)-CH_2-COOR^1 \quad (II.2)$$

$$R^1OOC-CH_2-CH_2-CH_2-CH_2-COOR^1 \quad (II.3).$$

24. The process according to claim 22, wherein the mixture of diester compounds of formula (II.1), (II.2) and (II.3) has the following composition:
from 75 to 95% by weight of the formula (II.1) compound,
from 3 to 23% by weight of the formula (II.2) compound,
from 0.1 to 10% by weight of the formula (II.3) compound.

25. A process for preparing an esteramide compound of following formula (I):

$$R^1OOC-A-CONR^2R^3 \quad (I)$$

comprising a reaction step between:
a diester compound of following formula (II):

$$R^1OOC-A-COOR^1 \quad (II)$$

and an amine of following formula (III):

$$HNR^2R^3 \quad (III)$$

in the presence of a basic compound,
formulae in which:
- A is a covalent bond or a straight-chain or branched divalent alkylene group comprising a number of carbon atoms ranging from 1 to 12,
- $R^1$ is an optionally substituted hydrocarbon group, comprising from 1 to 36 carbon atoms,
- $R^2$ and $R^3$, the same or different, are groups chosen from the hydrogen atom and the hydrocarbon groups, optionally substituted, comprising from 1 to 36 carbon atoms,
- $R^2$ and $R^3$ are able together to form a ring comprising the nitrogen atom with which they are linked, the said ring optionally being substituted and/or comprising an additional heteroatom, and
- $R^2$ and $R^3$ not simultaneously being hydrogen atoms, wherein:
the amine of formula (III) in gaseous form and the basic compound are co-added to the diester compound of formula (II),
and
wherein the reaction is conducted at a temperature comprised from 45° C. to 65° C.

26. The process according to claim 25, wherein the diester compound of formula (II) is a mixture of diester compounds of following formulae (II.1), (II.2) and (II.3):

$$R^1OOC-CH(CH_3)-CH_2-CH_2-COOR^1 \quad (II.1)$$

$$R^1OOC-CH(CH_2-CH_3)-CH_2-COOR^1 \quad (II.2)$$

$$R^1OOC-CH_2-CH_2-CH_2-CH_2-COOR^1 \quad (II.3).$$

27. The process according to claim 25, wherein the mixture of diester compounds of formula (II.1), (II.2) and (II.3) has the following composition:
- from 75 to 95% by weight of the formula (II.1) compound,
- from 3 to 23% by weight of the formula (II.2) compound,
- from 0.1 to 10% by weight of the formula (II.3) compound.

\* \* \* \* \*